US011213417B2

United States Patent
Piercy et al.

(10) Patent No.: US 11,213,417 B2
(45) Date of Patent: *Jan. 4, 2022

(54) LOWER-LEG EXOSKELETON SYSTEM AND METHOD

(71) Applicant: ROAM ROBOTICS INC., San Francisco, CA (US)

(72) Inventors: Brenton Piercy, San Francisco, CA (US); Tim Swift, Albany, CA (US); Giancarlo Nucci, San Francisco, CA (US); Callum Lamb, San Bruno, CA (US); Pete Lynn, Oakland, CA (US); Saul Griffith, San Francisco, CA (US); Leanne Luce, San Francisco, CA (US)

(73) Assignee: ROAM ROBOTICS INC., San Francisco, CA (US)

( * ) Notice: Subject to any disclaimer, the term of this patent is extended or adjusted under 35 U.S.C. 154(b) by 42 days.

This patent is subject to a terminal disclaimer.

(21) Appl. No.: 16/708,122

(22) Filed: Dec. 9, 2019

(65) Prior Publication Data

US 2020/0138604 A1    May 7, 2020

Related U.S. Application Data

(63) Continuation of application No. 15/082,824, filed on Mar. 28, 2016, now Pat. No. 10,543,110.

(Continued)

(51) Int. Cl.
*A61F 5/01*  (2006.01)
*A61F 2/60*  (2006.01)
(Continued)

(52) U.S. Cl.
CPC ............ *A61F 5/0127* (2013.01); *A43B 13/20* (2013.01); *A61F 2/60* (2013.01); *A61F 2/70* (2013.01);
(Continued)

(58) Field of Classification Search
CPC ............ A61F 2002/501; A61F 2002/74; A61F 2002/745; A61H 2205/106;
(Continued)

(56) References Cited

U.S. PATENT DOCUMENTS

| 440,684 A | 11/1890 | Yagn |
|---|---|---|
| 3,823,711 A | 7/1974 | Hatton |

(Continued)

FOREIGN PATENT DOCUMENTS

| CN | 104582668 A | 4/2015 |
|---|---|---|
| CN | 105205436 A | 12/2015 |

(Continued)

OTHER PUBLICATIONS

International Search Report and Written Opinion dated Apr. 26, 2018, International Patent Application No. PCT/US2018/016729, filed Feb. 2, 2018, 7 pages.

(Continued)

*Primary Examiner* — Timothy A Stanis
*Assistant Examiner* — Matthew R Moon
(74) *Attorney, Agent, or Firm* — Davis Wright Tremaine LLP

(57) ABSTRACT

A lower-leg exoskeleton that includes an inflatable actuator configured to be worn over a front portion of a leg of a user and configured to be disposed directly adjacent to and surrounding a joint of the leg of the user. The inflatable actuator is configured, when worn by the user, to receive and transmit an actuator load generated by the inflatable actuator around the joint of the user to a load contact point. Inflation of the inflatable actuator generates a moment about the joint of the user to cause flexion of the leg of the user.

17 Claims, 3 Drawing Sheets

Related U.S. Application Data

(60) Provisional application No. 62/139,184, filed on Mar. 27, 2015.

(51) Int. Cl.

| | | |
|---|---|---|
| *A61H 3/00* | (2006.01) | |
| *A61H 1/02* | (2006.01) | |
| *A43B 13/20* | (2006.01) | |
| *A61F 2/70* | (2006.01) | |
| *A61F 2/50* | (2006.01) | |
| *A61F 2/74* | (2006.01) | |

(52) U.S. Cl.
CPC ............. *A61H 1/0266* (2013.01); *A61H 3/00* (2013.01); *A61F 2/74* (2021.08); *A61F 2002/501* (2013.01); *A61F 2005/0155* (2013.01); *A61H 2003/007* (2013.01); *A61H 2201/0103* (2013.01); *A61H 2201/1238* (2013.01); *A61H 2201/1409* (2013.01); *A61H 2201/165* (2013.01); *A61H 2201/5007* (2013.01); *A61H 2201/5061* (2013.01); *A61H 2201/5069* (2013.01); *A61H 2205/106* (2013.01); *A61H 2205/12* (2013.01); *A61H 2230/207* (2013.01); *A61H 2230/30* (2013.01); *A61H 2230/50* (2013.01); *A61H 2230/60* (2013.01)

(58) Field of Classification Search
CPC .......... A61H 2205/12; A61H 2230/207; A61H 2230/30; A61H 2205/50; A61H 2230/60; A61H 9/005; A61H 9/0078; A61H 9/0085; A61H 3/00; A61H 2003/007; A61H 2201/01034; A61H 2201/1238; A61H 2201/165; A61H 2201/5007; A61H 2201/5058; A61H 2201/5061; A61H 2201/5064; A61H 2201/5069
See application file for complete search history.

(56) References Cited

U.S. PATENT DOCUMENTS

| | | | |
|---|---|---|---|
| 3,868,952 A | 3/1975 | Hatton | |
| 3,982,531 A | 9/1976 | Shaffer | |
| 3,993,056 A | 11/1976 | Rabischong et al. | |
| 4,274,399 A * | 6/1981 | Mummert | A61H 1/0288 601/40 |
| 4,523,582 A * | 6/1985 | Barber | A61H 1/0218 482/144 |
| 4,671,258 A | 6/1987 | Barthlome | |
| 4,944,755 A | 7/1990 | Hennequin et al. | |
| 5,033,457 A | 7/1991 | Bonutti | |
| 5,483,838 A | 1/1996 | Holden | |
| 7,086,322 B2 | 8/2006 | Schulz | |
| 7,479,121 B2 | 1/2009 | Branch | |
| 8,171,570 B2 | 5/2012 | Adarraga | |
| 8,784,350 B2 | 7/2014 | Cohen | |
| 9,205,560 B1 | 12/2015 | Edsinger et al. | |
| 9,821,475 B1 | 11/2017 | Lynn et al. | |
| 9,995,321 B2 | 6/2018 | Lynn et al. | |
| 10,012,229 B2 | 7/2018 | Lynn et al. | |
| 10,245,204 B2 | 4/2019 | Sandler et al. | |
| 10,543,110 B2 * | 1/2020 | Piercy | A61H 1/0266 |
| 10,562,180 B2 | 2/2020 | Telleria et al. | |
| 10,605,365 B1 | 3/2020 | Griffith et al. | |
| 10,619,633 B2 | 4/2020 | Lynn et al. | |
| 2001/0029343 A1 | 10/2001 | Seto et al. | |
| 2002/0026794 A1 | 3/2002 | Shahinpoor et al. | |
| 2004/0010720 A1 | 1/2004 | Singh et al. | |
| 2006/0069336 A1 | 3/2006 | Krebs et al. | |
| 2006/0161220 A1 | 7/2006 | Kobayashi et al. | |
| 2006/0173552 A1 | 8/2006 | Roy | |
| 2007/0042710 A1 | 2/2007 | Mahini et al. | |
| 2008/0009771 A1 | 1/2008 | Perry et al. | |
| 2008/0161937 A1 | 7/2008 | Sankai | |
| 2008/0195005 A1 | 8/2008 | Horst et al. | |
| 2008/0234608 A1 | 9/2008 | Sankai | |
| 2008/0287850 A1 | 11/2008 | Adarraga | |
| 2010/0114329 A1 | 5/2010 | Casler et al. | |
| 2010/0204627 A1 | 8/2010 | Kazerooni et al. | |
| 2010/0249675 A1 | 9/2010 | Fujimoto et al. | |
| 2010/0280424 A1 | 11/2010 | Kawakami et al. | |
| 2011/0071417 A1 | 3/2011 | Liu et al. | |
| 2011/0118635 A1 * | 5/2011 | Yamamoto | A61H 1/0237 601/5 |
| 2012/0059291 A1 | 3/2012 | Nguyen | |
| 2012/0289870 A1 | 11/2012 | Hsiao-Wecksler et al. | |
| 2013/0150980 A1 | 6/2013 | Swift et al. | |
| 2013/0158445 A1 | 6/2013 | Kazerooni et al. | |
| 2013/0245512 A1 | 9/2013 | Goffer et al. | |
| 2013/0289452 A1 * | 10/2013 | Smith | A63B 21/00181 601/33 |
| 2014/0109560 A1 | 4/2014 | Ilievski et al. | |
| 2014/0207037 A1 | 7/2014 | Horst | |
| 2014/0276264 A1 | 9/2014 | Caires et al. | |
| 2014/0277739 A1 | 9/2014 | Kornbluh et al. | |
| 2014/0318118 A1 | 10/2014 | Mazzeo et al. | |
| 2015/0088043 A1 | 3/2015 | Goldfield et al. | |
| 2015/0126911 A1 * | 5/2015 | Abramowicz | A61H 1/00 601/5 |
| 2015/0173993 A1 | 6/2015 | Walsh et al. | |
| 2015/0209214 A1 | 7/2015 | Herr et al. | |
| 2015/0290794 A1 | 10/2015 | Griffith et al. | |
| 2015/0351995 A1 | 12/2015 | Zoss et al. | |
| 2016/0107309 A1 | 4/2016 | Walsh et al. | |
| 2016/0158087 A1 | 6/2016 | Huang et al. | |
| 2016/0213548 A1 | 7/2016 | John et al. | |
| 2016/0261224 A1 | 9/2016 | Madrone et al. | |
| 2016/0278948 A1 | 9/2016 | Piercy et al. | |
| 2016/0297504 A1 | 10/2016 | Saindon et al. | |
| 2016/0300156 A1 | 10/2016 | Bowers et al. | |
| 2016/0331557 A1 | 11/2016 | Tong et al. | |
| 2016/0331624 A1 | 11/2016 | Sankai et al. | |
| 2017/0049587 A1 | 2/2017 | Herr et al. | |
| 2018/0079071 A1 | 3/2018 | Griffith et al. | |
| 2018/0086178 A1 | 3/2018 | Stanek et al. | |
| 2018/0125152 A1 | 5/2018 | Bruel | |
| 2018/0221237 A1 | 8/2018 | Swift et al. | |
| 2018/0235830 A1 | 8/2018 | Rokosz et al. | |
| 2018/0283414 A1 | 10/2018 | Lynn et al. | |
| 2018/0296625 A1 | 10/2018 | Lamb et al. | |
| 2019/0015233 A1 | 1/2019 | Galloway et al. | |
| 2019/0029918 A1 | 1/2019 | Inada et al. | |
| 2019/0060156 A1 | 2/2019 | Swift et al. | |
| 2019/0060157 A1 | 2/2019 | Lamb et al. | |
| 2019/0283235 A1 | 9/2019 | Nam et al. | |
| 2019/0307583 A1 | 10/2019 | Herr et al. | |
| 2019/0328604 A1 | 10/2019 | Contreras-Vidal et al. | |
| 2019/0383313 A1 | 12/2019 | Fowler et al. | |
| 2020/0253808 A1 | 8/2020 | Swift et al. | |

FOREIGN PATENT DOCUMENTS

| | | |
|---|---|---|
| CN | 204814712 U | 12/2015 |
| CN | 105264255 A | 1/2016 |
| CN | 105590409 A | 5/2016 |
| CN | 105992554 A | 10/2016 |
| CN | 106029039 A | 10/2016 |
| CN | 106413998 A | 2/2017 |
| CN | 111135031 A | 5/2020 |
| EP | 2827809 A1 | 1/2015 |
| EP | 3173191 A2 | 5/2017 |
| FR | 1463850 A | 7/1966 |
| JP | 362501723 A | 7/1987 |
| JP | 363199965 A | 8/1988 |
| JP | 2000051289 A | 2/2000 |
| JP | 2007282991 A | 11/2007 |
| WO | 9722782 A1 | 6/1997 |
| WO | 0004852 A1 | 2/2000 |
| WO | 2015080596 A1 | 6/2015 |
| WO | 2015104832 A1 | 7/2015 |

(56) References Cited

FOREIGN PATENT DOCUMENTS

| WO | 2016166442 | A1 | 10/2016 |
|----|------------|----|---------|
| WO | 2016166588 | A1 | 10/2016 |
| WO | 2016207855 | A1 | 12/2016 |
| WO | 2017110453 | A1 | 6/2017 |
| WO | 2018218336 | A1 | 12/2018 |
| WO | 2019183397 | A1 | 9/2019 |
| WO | 2019187030 | A1 | 10/2019 |

OTHER PUBLICATIONS

International Search Report and Written Opinion dated Dec. 6, 2018, International Patent Application No. PCT/US2018/048638, filed Aug. 29, 2018, 8 pages.
International Search Report and Written Opinion dated Dec. 6, 2018, Patent Application No. PCT/US2018/048639, 7 pages.
International Search Report and Written Opinion dated Jul. 18, 2016, International Patent Application No. PCT/US2016/024366, filed Mar. 25, 2016, 7 pages.
International Search Report and Written Opinion dated Jul. 19, 2018, International Patent Application No. PCT/US2018/027643, filed Apr. 13, 2018, 7 pages.
International Search Report and Written Opinion dated Mar. 30, 2021, Patent Application No. PCT/US2020/064647, 10 pages.
Tamez-Duque et al., "Real-time strap pressure sensor system for powered exoskeletons," Sensors 15(2):4550-4563, Feb. 2015.
Taniguchi, "Flexible Artificial Muscle Actuator Using Coiled Shape 5 Memory Alloy Wires," APCBEE Procedia 7:54-59, Jan. 1, 2013.
Huang et al., "Interactive learning for sensitivity factors of a human-powered augmentation lower exoskeleton," 2015 IEEE/RSJ International Conference on Intelligent Robots and Systems (IROS), Sep. 28, 2015, 7 pages.
International Search Report and Written Opinion dated Aug. 26, 2021, Patent Application No. PCT/US2021/034447, 7 pages.
International Search Report and Written Opinion dated Jun. 3, 2021, Patent Application No. PCT/US2021/019711, 12 pages.
International Search Report and Writtent Opinion dated Aug. 26, 2021, Patent Application No. PCT/US2021/034468, 8 pages.
International Search Report and Written Opinion dated Aug. 26, 2021, Patent Application No. PCT/US2021/034444, 7 pages.
International Search Report and Written Opinion dated Aug. 26, 2021, Patent Application No. PCT/US2021/034593, 10 pages.
International Search Report and Written Opinion dated Sep. 2, 2021, Patent Application No. PCT/US2021/034030, 9 pages.
International Search Report and Written Opinion dated Sep. 2, 2021, Patent Application No. PCT/US2021/034450, 9 pages.
International Search Report and Written Opinion dated Sep. 9, 2021, Patent Application No. PCT/US2021/034443, 8 pages.
International Search Report and Written Opinion dated Sep. 9, 2021, Patent Application No. PCT/US2021/034579, 8 pages.

* cited by examiner

LOWER-LEG EXOSKELETON SYSTEM AND METHOD

CROSS-REFERENCE TO RELATED APPLICATIONS

This application is a continuation of U.S. application Ser. No. 15/082,824, filed Mar. 28, 2016, which is a nonprovisional of and claims the benefit of U.S. Provisional Application No. 62/139,184 filed Mar. 27, 2015, which applications are hereby incorporated herein by reference in their entirety and for all purposes.

GOVERNMENT RIGHTS

This invention was made with government support under SOCOM—H9222-15-C-0017 awarded by the United States Special Operations Command, and NASA—NNX14CA56P awarded by National Aeronautics and Space Administration. The government has certain rights in the invention.

BACKGROUND

Exoskeletons can be beneficial in assisting disabled users with mobility and can also be beneficial in providing users with strength assistance or providing extra-human abilities. For example, where disabled users lack control over certain parts of their body or have reduced strength in certain body parts, an exoskeleton can be used to regain mobility or increase strength in such body parts. In another example, an exoskeleton can be used to assist users in tasks such as lifting or carrying heavy objects, which can increase the stamina of the user or provide the user with additional strength.

Exoskeletons can be coupled with various portions of the body including the arms, legs, torso, head, hands and feet. However, conventional leg exoskeletons often use an interface between the exoskeleton appendage and the user's foot that is sloppy. Furthermore, force transmission is generally effected via a contact point at the heel, which can lead to a nonstandard gait, and limit actions such as squatting.

In view of the foregoing, a need exists for an improved lower-leg exoskeleton system and method in an effort to overcome the aforementioned obstacles and deficiencies of conventional exoskeleton systems.

Figure 1:
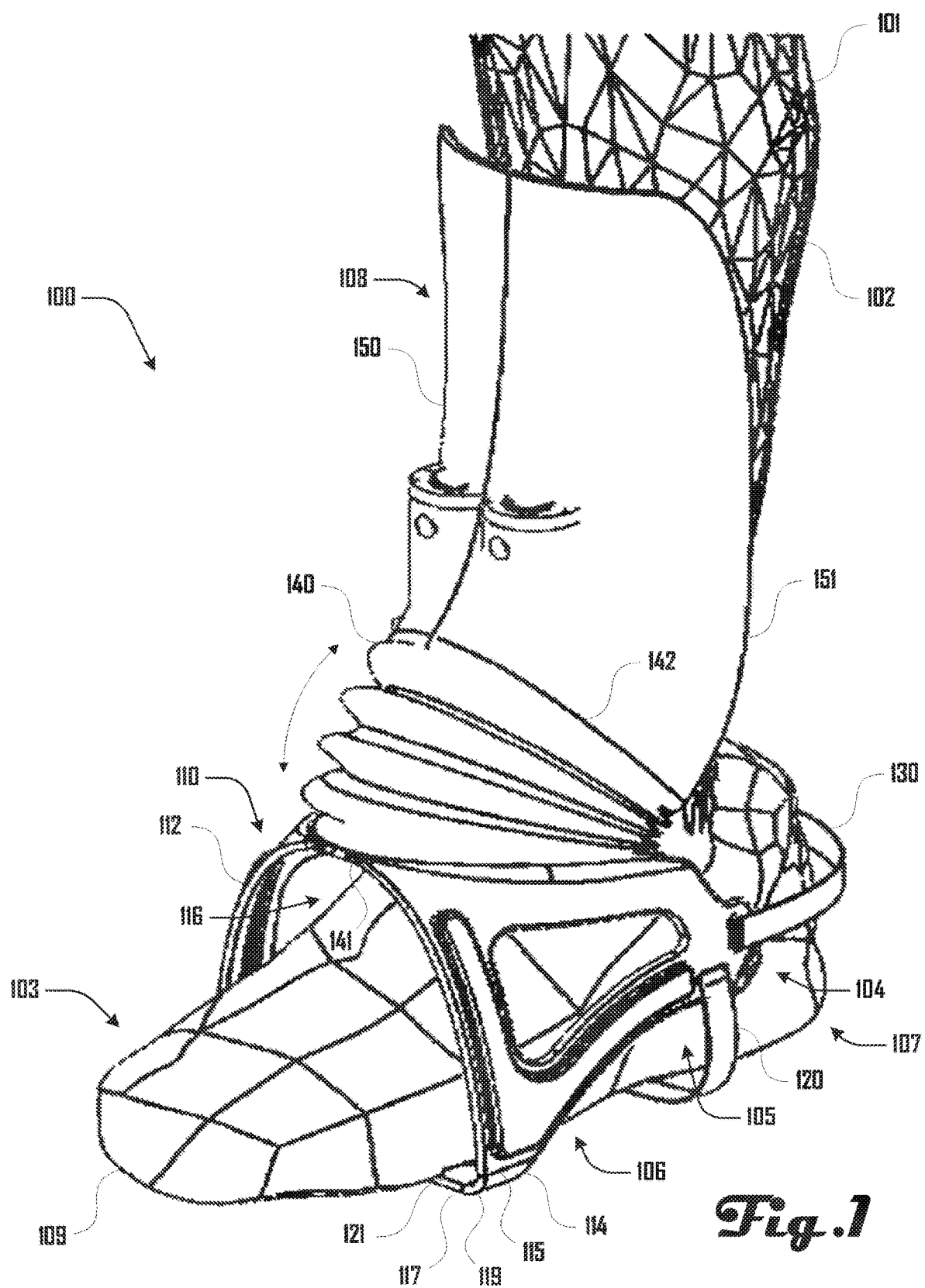
FIG. 1 is an exemplary perspective illustration of a lower-leg exoskeleton being worn by a user in accordance with an embodiment.

It should be noted that the figures are not drawn to scale and that elements of similar structures or functions are generally represented by like reference numerals for illustrative purposes throughout the figures. It also should be noted that the figures are only intended to facilitate the description of the preferred embodiments. The figures do not illustrate every aspect of the described embodiments and do not limit the scope of the present disclosure.

DETAILED DESCRIPTION OF THE PREFERRED EMBODIMENTS

The following disclosure illustrates example embodiments pertaining to the design of novel exoskeleton orthotics for the ankle, foot, and ankle-foot interface, as well as methods for attaching to and transmitting power through users' feet and/or footwear. Connection to the feet has remained an unsolved problem in exoskeleton development and various systems methods described herein are designed to minimize user discomfort through the use of semi-compliant and/or dynamically adjustable structures, while maintaining a sufficiently rigid force transmission path to allow for efficient power output and control.

The present disclosure teaches the design and implementation of various example embodiments of a shoe/orthosis that can work as a standalone unit, or can be integrated into a robotic exoskeleton in order to provide control of the ankle. Various preferred embodiments include a structure that allows force to be transmitted directly through the sole of a piece of footwear, without using the user's foot as part of the load path. To accomplish this, in some embodiments, footwear associated with an ankle actuator can be modified or specially designed. It can be beneficial for components within the sole of the shoe to be configured to receive and transmit actuator load without interfering with the user's movements or causing damage to the shoe. For example, some embodiments can include a load contact point forward of the heel of a user, such as at or forward of the tarsals or metatarsals.

One embodiment can comprise a specially designed substructure built into the sole, with exposed external attachment points to create an interface with an exoskeleton. These connection points can have quick-connect attachments to make it easier for the user to put on the device. These attachment points can be retractable to further improve ease of use when putting on or taking off the device. The shoe sole substructure can be rigid, and/or have a dynamically adjustable stiffness by way of inflatable structures and/or smart materials. In some embodiments, additional structures in the sole can be used to transmit the exoskeleton's load evenly across the ground, and can be dynamically adjustable to compensate for changes in gait due to different operating conditions (movement speed, terrain, etc.). Accordingly, various example embodiments described herein are configured for more comfortable power transmission through the ankle and provided better range of motion compared to conventional exoskeletons.

Turning to FIG. 1, an example lower-leg exoskeleton 100 is shown coupled to a user 101 about the leg 102, including the foot 103 and ankle 104. In this example, the lower-leg exoskeleton 100 is shown coupled about the tarsals 105, metatarsals 106, heel 107 and shin 108.

The lower-leg exoskeleton 100 is shown comprising a foot structure 110 that is coupled to an actuator 140 at a first actuator end 141, and further comprising a shin structure 150 coupled at a second actuator end 142. The foot structure 110 is shown including sidewalls 112 and a base 114, which define a slot 116 in which the foot 103 of the user 101 can be disposed. A base strap 120 is illustrated being coupled to the foot structure 110 and encircling a portion of the foot 103. A heel strap 130 is illustrated being coupled to the foot structure 110 and encircling a portion of the heel 107.

In this example, the sidewalls 112 define a generally C-shaped portion of the foot structure 110 with the base 114 being substantially planar and engaging a bottom portion of the foot 103. The foot structure 110 can be rigid and comprise materials such as plastic, metal or the like. In various embodiments, the base 114 can provide a load-path contact point forward of the heel 107 of a user, such as at or forward of the tarsals 105 or metatarsals 106.

In further embodiments, the foot structure 110 can comprise and/or be defined by inflatable structures that surround portions of the foot 103, including the tarsals 105 and/or metatarsals 106. In other words, structures such as the sidewalls 112, base 114, base strap 120, heel strap 130, or the like, can comprise an inflatable structure. In one example, inflatable structures can be positioned on the sole of the foot 103, which can be configured to spread a load generated while walking evenly across the ground or other surface being walked on.

Although the foot structure 110 is shown in one example configuration in FIG. 1, it should be clear that various other suitable configuration of a foot structure 110 are within the scope and spirit of the present disclosure. For example, a rigid superstructure can attach beneath the sole of the foot 103 and can skirt around the foot 103 to provide a force transmission platform above the foot 103.

In further embodiments, the lower-leg exoskeleton 100 can be configured to be worn over clothing and/or footwear such as a conventional boot, shoe, or the like. However, in some embodiments, a portion of the lower-leg exoskeleton 100 can be disposed in, comprise, or be integrally coupled with a boot, shoe, or the like. In other words, some examples provide specialized footwear for use with the lower-leg exoskeleton 100, which can incorporate portions of the lower-leg exoskeleton 100 or otherwise be specifically configured to be used with or coupled with the lower-leg exoskeleton 100. For example, structures such as the sidewalls 112, base 114, base strap 120, heel strap 130, or the like, can be disposed in or be defined by a portion of a shoe or boot.

In another embodiment, a boot or shoe can comprise a segmented structure that comprises a system of rigid panels connected by a flexible joint (e.g., an elastomer) that allows for in-plane rotation, (e.g., in the plane described as where the ankle rotates towards and away from the shin), and/or lateral motion. In a further embodiment, a structure in the heel of a shoe or boot can be configured to provide a load path for a reaction force that acts to lift the heel 107 of the user 101.

FIG. 1 illustrates an example composite structure that can act as an ankle actuation and passive support structure for a single sided, single degree-of-freedom (DOF) ankle actuator. The example configuration shown in FIG. 1 comprises an inflatable actuator 140 coupled with rigid passive components (e.g., the foot structure 110 and the shin structure 150) to transfer torque generated by the actuator 140 to the user 101. Accordingly, in various embodiments, one or more rigid components associated with the sole of the foot 103 can be of sufficient in strength to take the load of the actuator 140. In various embodiments as described in further detail herein, the inflatable actuator 140 can provide a moment about the ankle 104 of the user 101. For example, the foot structure 110 can be connected via a feature in the sole of a shoe that allows the user 101 to dorsiflex and/or plantar flex his or her foot 103.

Plantarflexion torque can be provided by inflating the actuator 140. In this example configuration, the actuator 140 may only connect to the footwear at a load transmission point, but this should not be construed to limit the many alternative embodiments of the design. Other versions of this system can be integrated in various suitable ways. For example, in some cases, the actuator 140 and footwear can encompass a single piece of hardware that is designed for a specific user (or for a specific size leg and foot), and thus can be smaller in some embodiments.

In some embodiments the rigid foot structure 110 comprises: a pair of sidewalls 112 configured to extend around the foot 103 of a user 101 and including first and second sidewall attachment points 115 respectively on the sidewalls 112 for attachment with a removable base portion 117, and a removable flat base portion 117 configured to reside at the base of the foot of the user that includes first and second base attachment points 119 configured for removably coupling with the first and second sidewall attachment points, the removable flat base portion 117 integrally disposed within and extending through the sole of a footwear article 109 with the first and second base attachment points 119 disposed on respective external sides of the footwear article 109.

In some embodiments, the rigid foot structure 110 further comprises an inflatable structure 121. In some embodiments, an inflatable structure 121 is positioned at the sole of a foot of a user and configured to evenly spread a load on a surface generated while the user is walking on the surface. In some embodiments, the rigid shin structure further comprises an inflatable structure 151.

Figure 2:
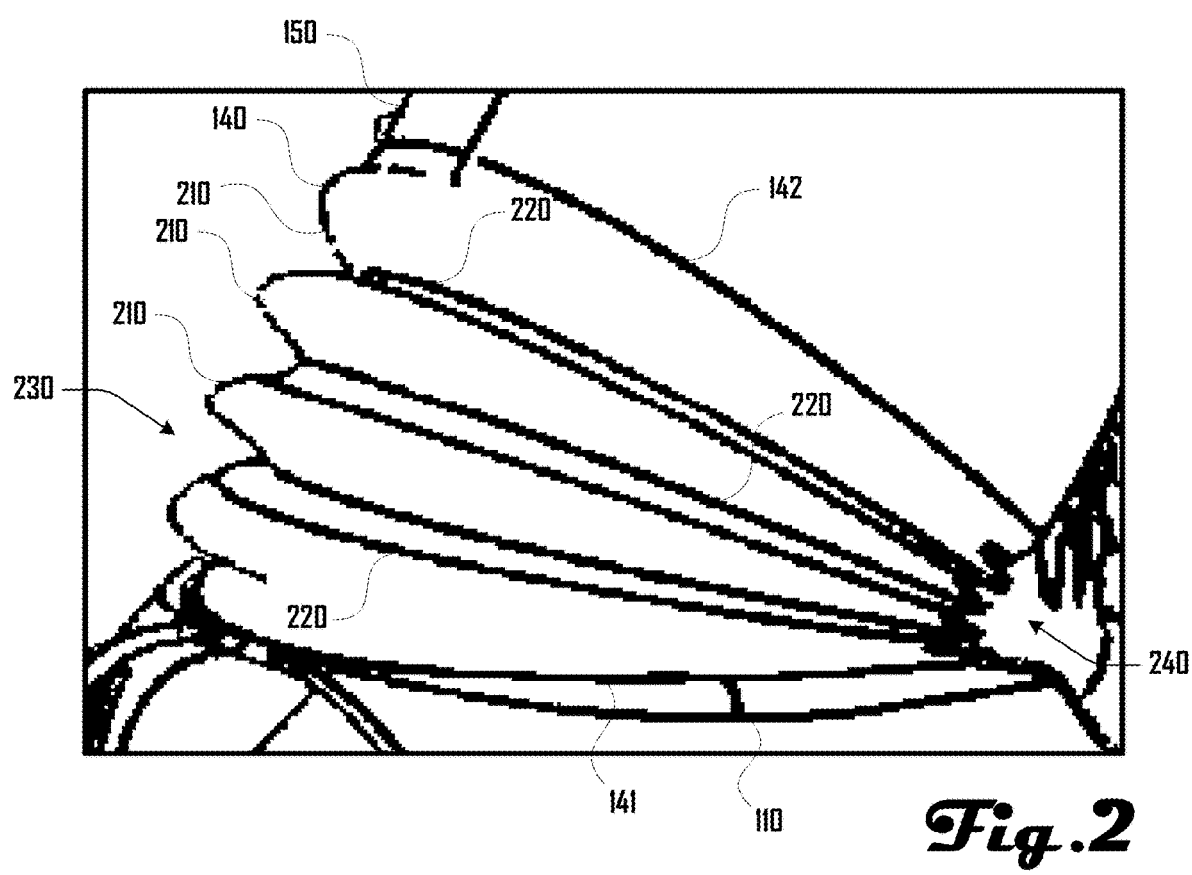
FIG. 2 is an exemplary close-up illustration of an inflatable actuator of the example embodiment of FIG. 1.

FIG. 2 depicts a close-up view of the inflatable actuator 140 of FIG. 1, which illustrates that the example actuator 140 can comprise a plurality of stacked inflatable bladder segments 210, which are separated by a plurality of collars 220 that are stacked between respective bladder segments 210. In some embodiments, the bladder segments 210 can comprise internally separate cavities or can comprise an internally interconnected cavity. For example, in some embodiments, the collars 220 can physically separate respective internal cavities of respective bladder segments 210. In some embodiments, the collars 220 can be defined by a seam, pucker, or the like. In further embodiments, the collars 220 can be absent.

As illustrated in FIGS. 1 and 2, the bladder segments 210 and collars 220 can extend around and surround a front portion of the foot 103 of a user 101. More specifically, the bladder segments 210 and collars 220 can extend from a front portion 230 to rear portions 240 at the side or rear of the foot 103. Inflation of the bladder segments 210 can result in expansion of the bladder segments 210, and in this example, the actuator 140 can be configured for larger expansion at the front portion 230 relative to the rear portions 240.

Accordingly, the inflatable actuator 140 can provide a moment about the ankle 104 of the user 101 due to the difference in expansion of the bladder segments 210 between the front and rear portions 230, 240. For example, inflation of the actuator 140 can generate a moment that forces the shin structure 150 toward the shin 108 of the user, and a moment that generates plantar flexion of the foot 103. In other words, the shin structure 150 engaging the shin 108 opposes the actuator 140 such that a rotation generated by the actuator 140 during inflation results in rotation of the foot 103. Additionally, the collars 220 can provide for stabilization of the bladder segments 210, which can generate uniform expansion of the actuator 140 while being inflated.

Although a generally C-shaped inflatable actuator 140 is illustrated in the example embodiment of FIGS. 1 and 2, in further embodiments, other suitable actuators and actuator configurations can be used. For example, in one embodiment, an actuator 140 can be powered in other suitable ways including via a motor, or the like. Additionally, in another example, an actuator can include elongated segments positioned along the length of the shin 108 at the front of the foot 103, which can be configured to expand and curl lengthwise to generate a moment that causes plantar flexion of the foot 103. In a further example, an actuator 140 can completely surround the foot 103. Accordingly, it should be clear that the example actuator 140 illustrated in this disclosure should not be construed to be limiting on the many alternative actuators that are within the scope and spirit of the present invention.

Figure 3:
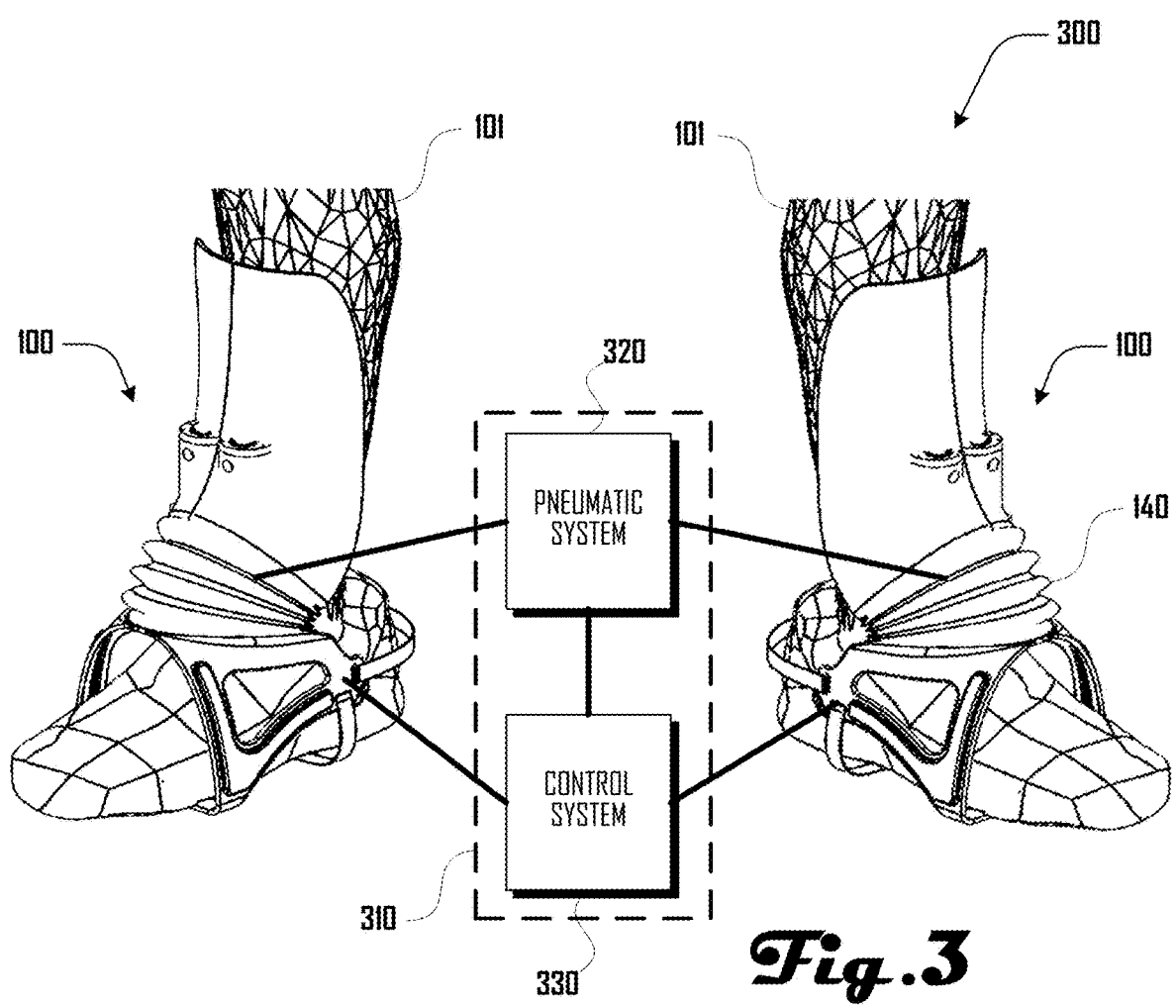
FIG. 3 illustrates an exoskeleton system that comprises a first and second lower-leg exoskeleton that are operably connected to an actuation system that includes a pneumatic system and a control system.

FIG. 3 illustrates an exoskeleton system 300 that comprises a first and second lower-leg exoskeleton 100 that are operably connected to an actuation system 310 that includes a pneumatic system 320 and a control system 330. The pneumatic system 320 is shown being operably connected to the actuators 140 and to the control system 330. The control system 330 is illustrated being operably connected to one or more portions of the lower-leg exoskeletons 100 and to the pneumatic system 320.

In various embodiments, the pneumatic system 320 can be configured to inflate and/or deflate the actuators 140 with a fluid. For example, in one embodiment, the pneumatic system 320 can only be configured to actively inflate the actuators 140 to cause expansion of the actuators 140 and plantar flexion, where deflation can be generated during contact with the ground during walking and where natural dorsiflexion occurs. In another embodiment, the pneumatic system 320 can be configured to actively inflate the actuators 140 to cause expansion of the actuators 140 and plantar flexion, and can actively generate dorsiflexion by actively evacuating fluid from the actuators 140 and/or by generating release of fluid from the actuators 140.

Alternatively, in some embodiments, the actuators can be configured oppositely. For example, inflation of the actuator 140 can cause dorsiflexion of the foot 103 and deflation can cause or be caused by plantar flexion of the foot 103. Additionally, although the example of a pneumatic system 320 is provided, which actuates the actuators 140 via a gas fluid (e.g., air), in further embodiments, the actuators 140 can operate via any suitable fluid, including water, oil, or the like.

In some embodiments, inflatable actuators can be positioned in other locations in addition to or alternatively to the inflatable actuator 140 illustrated in FIGS. 1-3. For example, one or more actuator can be positioned about the sole of the foot 103, at the heel 107, or the like. Such additional or alternative actuators can be configured to generate various types of movement of the foot 103, including inversion, eversion, plantar flexion, dorsiflexion, flexion of a toe, extension of a toe, and the like. Additionally, various suitable portions of a lower-leg exoskeleton 100 can comprise inflatable support structures as discussed herein.

The control system 330 can be associated with various suitable portions of the lower-leg exoskeleton 100 and can be associated with one or more suitable sensors. For example, sensors can determine a position, movement, rotation or orientation of the foot 103 and/or portion of the lower-leg exoskeleton 100. Additionally, and alternatively, such sensors can determine an inflation state of an actuator 140, a pressure associated with an actuator 140, or the like. Additionally, and alternatively, such sensors can measure body and/or environmental conditions such as temperature, moisture, salinity, blood pressure, oxygen saturation, muscle tension, and the like.

In various embodiments, the control system 330 can sense conditions associated with the lower-leg exoskeletons 100 and inflate and/or deflate the actuators 140 in response. In some embodiments, the control system 330 can generate a walking gait for a user 101 of the lower-leg exoskeletons 100 by selective inflation and/or deflation of the actuators 140. In other embodiments, the control system 330 can identify and support movements of a user 101 associated with the lower-leg exoskeletons 100. For example, the control system 330 can determine that a user 101 is lifting a heavy object and provide enhancing support to the user 101 in lifting the object by selective inflation and/or deflation of the actuators 140.

Accordingly, the present example embodiment shown in FIGS. 1-3 should not be construed to be limiting on the wide variety of alternative embodiments that are within the scope and spirit of the present invention. For example, in some embodiments, the control system 330 can comprise sensors such as ground reaction force sensors embedded in the sole of the shoe along with pressure and angle sensors to measure the effort of the actuation. Muscle activation sensors can also be integrated into footwear to allow for feedback control by the control system 330.

A further embodiment of the sole design can incorporate an actuator directly into the sole of an article worn by a user. Such an actuator can work as a standalone device or in concert with other portions of a lower-leg exoskeleton 100 to provide motive force by direct manipulation of the sole.

To anchor the forefoot in place and transmit load to the sole, structures can be built around the tarsal 105 and metatarsal 106 areas of the foot 103 in accordance with various embodiments. For example, in one embodiment, these structures can be simple rigid structures (which can be solid structures, and/or passive inflatable structures) that provide a repeatable load path. In other iterations, such structures can be dynamically adjustable via the use of smart materials; by adjusting the pressure of inflatable chambers; and the like.

As loading in some embodiments occurs at or near the ball of the foot 103, additional structure(s) can be added in some embodiments to the heel area 107, to help ensure that ankle 104 pivoting occurs in the desired location, to provide stability, and the like. In some embodiments, an ankle actuator 140 can comprise a two part, antagonistic design. For example, a pair of actuators 140 can provide a load path for force creating dorsiflexion and/or plantar flexion via inflation and/or deflation of the actuators 140.

In further embodiments, especially those designed for high performance (high speed, high force output), the shin structure 150 can be beneficial to distribute the force created by the ankle actuator 140 as discussed herein. This shin structure 150 can be built into the actuator 140, and connect to set attachment points on an article worn by a user, or the article can have an integrated shin support or shin structure 150. The shin structure can include rigid and/or inflated passive structures positioned over the shin 108 to distribute load to the shin 108 during actuation of the lower-leg exoskeletons 100.

To connect rigid structures above and below the ankle, flexible materials can be used to create a pivot that allows for both lateral movement and rotation of the shin relative to the ankle. In some embodiments, some or all force transmission structures can be created through the use of passively inflated structures, which can be deflated to allow for a comfortable and un-intrusive resting state when the system is not in active use. Additionally, by integrating attachment points, sensing, and load transfer structures directly into footwear, and transmitting force through the ball of the foot in accordance with some embodiments, it is possible to create a more efficient system that is less intrusive and more comfortable for the user.

One embodiment can comprise a specially designed substructure built into the sole, with exposed external attachment points to create an interface with an exoskeleton. These connection points can have quick-connect attachments to make it easier for the user to put on the device. These attachment points can be retractable to further improve ease of use when putting on or taking off the device. The shoe sole substructure can be rigid.

For example, referring to FIG. 1, in one embodiment, the base portion 114 of the foot structure 110 can be removable from the sidewalls 112 via first and second attachments, which can any suitable attachment mechanism including a hook, slot, bolt, clip, knob, or the like. In some embodiments, the base portion 114 can be integrally disposed within or affixed within footwear such as a shoe or boot.

In other words, the removable base portion 114, having attachment point on a first and second end, can extend through the sole of a boot or shoe with the attachment points exposed on respective external sides of the shoe for attachment with a lower-leg exoskeleton 100. The attachment points can correspond to and be configured for coupling with attachment structures of the sidewalls 112 or the like. Such embodiments can be desirable and provide for quick attachment and detachment of the lower-leg exoskeleton 100 to and from conventional footwear.

In alternative embodiments, attachment points of the base portion 114 can be configured for attachment at various suitable positions in, on or about a shoe, boot, or the like. For example, in one embodiment attachment points of the base portion 114 can be positioned within a shoe or boot cavity. Such embodiments can be desirable for providing a connection with the lower-leg exoskeleton 100 which is less obtrusive and observable to others. In a further embodiment, the base portion 114 can comprise a rigid insert configured to be disposed over or within the insole of a shoe or boot and such an insert can comprise attachment points as discussed above or can be integrally attached to the sidewalls 112 or other suitable portion of a lower-leg exoskeleton 100

The described embodiments are susceptible to various modifications and alternative forms, and specific examples thereof have been shown by way of example in the drawings and are herein described in detail. It should be understood, however, that the described embodiments are not to be limited to the particular forms or methods disclosed, but to the contrary, the present disclosure is to cover all modifications, equivalents, and alternatives.

What is claimed is:

1. A lower-leg exoskeleton comprising:
   an inflatable actuator that is configured to be worn over a front portion of a foot of a user and configured to be disposed directly adjacent to and surrounding an ankle of the foot of the user; and
   a rigid foot structure coupled to a first actuator end of the inflatable actuator, configured to surround a portion of the foot of the user, wherein the rigid foot structure comprises:
      a pair of sidewalls configured to extend around the foot of the user and including first and second sidewall attachment points for connecting to a base portion, and
      a base portion configured to reside at a base of the foot of the user that includes first and second base attachment points coupling with the first and second sidewall attachment points; and
   wherein, the inflatable actuator and rigid foot structure are configured to, when worn by the user, receive and transmit an actuator load generated by the inflatable actuator around the foot of the user to a load contact point of the lower-leg exoskeleton configured to be disposed at a bottom of the foot of the user defined by the rigid foot structure and forward of a heel of the user; and
   wherein inflation of the inflatable actuator generates a moment about the ankle of the user to cause flexion of the foot of the user.

2. The lower-leg exoskeleton of claim 1, wherein the inflatable actuator is generally C-shaped and configured to be disposed directly adjacent to and surround the ankle of the foot of the user including a front of the ankle and peripheral sides of the ankle.

3. The lower-leg exoskeleton of claim 1, wherein the inflatable actuator is operably coupled with a fluidic system and is configured to be inflated by the fluidic system to generate the moment about the ankle of the user to cause flexion of the foot of the user.

4. The lower-leg exoskeleton of claim 1, wherein the inflatable actuator comprises a plurality of stacked bladder segments, the bladder segments stacked in horizontal rows disposed perpendicular to an axis of rotation of the ankle of the user.

5. A lower-leg exoskeleton comprising:
   an inflatable actuator that is configured to be worn over a front portion of a foot of a user and configured to be disposed directly adjacent to and surrounding an ankle of the foot of the user; and
   a rigid foot structure coupled to a first actuator end of the inflatable actuator, configured to surround a portion of the foot of the user,
   wherein, the inflatable actuator and rigid foot structure are configured to, when worn by the user, receive and transmit an actuator load generated by the inflatable actuator around the foot of the user to a load contact point of the lower-leg exoskeleton configured to be disposed at a bottom of the foot of the user defined by the rigid foot structure and forward of a heel of the user;
   wherein the rigid foot structure comprises a pair of sidewalls configured to extend around the foot of the user and including first and second sidewall attachment points for connecting to a base portion; and
   wherein inflation of the inflatable actuator generates a moment about the ankle of the user to cause flexion of the foot of the user.

6. The lower-leg exoskeleton of claim 5, wherein the inflatable actuator comprises a plurality of stacked bladder segments, the bladder segments stacked in horizontal rows disposed perpendicular to an axis of rotation of the ankle of the user.

7. A lower-leg exoskeleton comprising:
   an inflatable actuator that is configured to be worn over a front portion of a foot of a user and configured to be disposed directly adjacent to and surrounding an ankle of the foot of the user; and
   a rigid foot structure coupled to a first actuator end of the inflatable actuator, configured to surround a portion of the foot of the user,
   wherein, the inflatable actuator and rigid foot structure are configured to, when worn by the user, receive and transmit an actuator load generated by the inflatable actuator around the foot of the user to a load contact point of the lower-leg exoskeleton configured to be disposed at a bottom of the foot of the user defined by the rigid foot structure and forward of a heel of the user;

wherein inflation of the inflatable actuator generates a moment about the ankle of the user to cause flexion of the foot of the user; and wherein the rigid foot structure comprises a base portion configured to reside at a base of the foot of the user that includes first and second base attachment points coupling with first and second sidewall attachment points.

8. A lower-leg exoskeleton comprising:

an inflatable actuator that is configured to be worn over a front portion of a foot of a user and configured to be disposed directly adjacent to and surrounding an ankle of the foot of the user; and a rigid foot structure coupled to a first actuator end of the inflatable actuator, configured to surround a portion of the foot of the user, wherein, the inflatable actuator and rigid foot structure are configured to, when worn by the user, receive and transmit an actuator load generated by the inflatable actuator around the foot of the user to a load contact point of the lower-leg exoskeleton configured to be disposed at a bottom of the foot of the user defined by the rigid foot structure and forward of a heel of the user;

wherein inflation of the inflatable actuator generates a moment about the ankle of the user to cause flexion of the foot of the user; and wherein the inflatable actuator is generally C-shaped and configured to be disposed directly adjacent to and surround the ankle of the foot of the user including a front of the ankle and peripheral sides of the ankle.

9. A lower-leg exoskeleton comprising:

an inflatable actuator configured to be worn over a front portion of a leg of a user and configured to be disposed directly adjacent to and surrounding a joint of the leg of the user, wherein the inflatable actuator is configured to, when worn by the user, receive and transmit an actuator load generated by the inflatable actuator around the joint of the user to a load contact point of the lower-leg exoskeleton;

wherein the inflatable actuator is generally C-shaped and configured to be disposed directly adjacent to and surround an ankle of a foot of the user including a front of the ankle and peripheral sides of the ankle; and wherein inflation of the inflatable actuator generates a moment about the joint of the user to cause flexion of the leg of the user.

10. The lower-leg exoskeleton of claim 9, wherein the load contact point is configured to be disposed at a bottom of the foot of the leg of the user.

11. The lower-leg exoskeleton of claim 9, wherein the load contact point is configured to be disposed at the foot of the user and defined by a rigid foot structure, the load contact point is configured to be disposed forward of a heel of the user.

12. The lower-leg exoskeleton of claim 9, wherein the joint is an ankle of the foot of the user.

13. The lower-leg exoskeleton of claim 9, wherein the lower-leg exoskeleton further comprises a rigid structure coupled to a first actuator end of the inflatable actuator, the rigid structure configured to surround a portion of the user.

14. The lower-leg exoskeleton of claim 9, wherein the inflatable actuator comprises a plurality of stacked bladder segments, the bladder segments stacked in horizontal rows disposed perpendicular to an axis of rotation of the ankle of the user.

15. The lower-leg exoskeleton of claim 9, wherein the inflatable actuator is operably coupled with a fluidic system and is configured to be inflated by the fluidic system to generate the moment about the ankle of the user to cause flexion of the foot of the user.

16. A lower-leg exoskeleton comprising:

an inflatable actuator configured to be worn over a front portion of a leg of a user and configured to be disposed directly adjacent to and surrounding a joint of the leg of the user, wherein the inflatable actuator is configured to, when worn by the user, receive and transmit an actuator load generated by the inflatable actuator around the joint of the user to a load contact point of the lower-leg exoskeleton;

wherein inflation of the inflatable actuator generates a moment about the joint of the user to cause flexion of the leg of the user;

wherein the lower-leg exoskeleton further comprises a rigid structure coupled to a first actuator end of the inflatable actuator, the rigid structure configured to surround a portion of the joint of the user; and wherein the rigid structure comprises one or more sidewalls configured to extend around a foot of the user and including at least one sidewall attachment point for connecting to a base portion.

17. A lower-leg exoskeleton comprising:

an inflatable actuator configured to be worn over a front portion of a leg of a user and configured to be disposed directly adjacent to and surrounding a joint of the leg of the user, wherein the inflatable actuator is configured to, when worn by the user, receive and transmit an actuator load generated by the inflatable actuator around the joint of the user to a load contact point of the lower-leg exoskeleton;

wherein inflation of the inflatable actuator generates a moment about the joint of the user to cause flexion of the leg of the user;

wherein the lower-leg exoskeleton further comprises a rigid structure coupled to a first actuator end of the inflatable actuator, the rigid structure configured to surround a portion of the joint of the user; and wherein the rigid structure comprises a base portion configured to reside at a base of a foot of the user that includes one or more base attachment points that couple with one or more sidewall attachment points.

* * * * *